United States Patent
Bevinakatti

(10) Patent No.: US 10,016,352 B2
(45) Date of Patent: *Jul. 10, 2018

(54) HAIR FIXATIVES INCLUDING CELLULOSE ETHER BASED POLYGLUCOSE POLYMERS

(71) Applicant: Akzo Nobel Chemicals International B.V., Arnhem (NL)

(72) Inventor: Hanamanthsa Bevinakatti, Somerset, NJ (US)

(73) Assignee: Akzo Nobel Chemicals International B.V., Arnhem (NL)

( * ) Notice: Subject to any disclaimer, the term of this patent is extended or adjusted under 35 U.S.C. 154(b) by 15 days.

This patent is subject to a terminal disclaimer.

(21) Appl. No.: 15/101,198

(22) PCT Filed: Dec. 17, 2014

(86) PCT No.: PCT/EP2014/078229
§ 371 (c)(1),
(2) Date: Jun. 2, 2016

(87) PCT Pub. No.: WO2015/091652
PCT Pub. Date: Jun. 25, 2015

(65) Prior Publication Data
US 2016/0303023 A1 Oct. 20, 2016

Related U.S. Application Data

(60) Provisional application No. 61/919,116, filed on Dec. 20, 2013.

(30) Foreign Application Priority Data

Feb. 19, 2014 (EP) .................................. 14155802

(51) Int. Cl.
A61K 8/73 (2006.01)
A61K 8/34 (2006.01)
A61Q 5/06 (2006.01)
C08L 1/32 (2006.01)
C08B 11/20 (2006.01)
C08B 13/00 (2006.01)
C09J 101/32 (2006.01)

(52) U.S. Cl.
CPC ................ *A61K 8/731* (2013.01); *A61K 8/34* (2013.01); *A61Q 5/06* (2013.01); *C08B 11/20* (2013.01); *C08B 13/00* (2013.01); *C08L 1/32* (2013.01); *C09J 101/32* (2013.01); *A61K 2800/30* (2013.01)

(58) Field of Classification Search
None
See application file for complete search history.

(56) References Cited

U.S. PATENT DOCUMENTS

| | | | |
|---|---|---|---|
| 3,741,783 A | 6/1973 | Tunc | |
| 2002/0197225 A1 | 12/2002 | Giroud et al. | |
| 2010/0029928 A1* | 2/2010 | De Vries | A61K 8/046 536/109 |
| 2011/0064678 A1* | 3/2011 | Knappe | A61K 8/8152 424/47 |

FOREIGN PATENT DOCUMENTS

| | | |
|---|---|---|
| EP | 1240887 A1 | 9/2002 |
| EP | 1240888 A1 | 9/2002 |
| FR | 2778559 A1 | 11/1999 |
| JP | 2002-265323 A | 9/2002 |
| WO | 99/059532 A1 | 11/1999 |

OTHER PUBLICATIONS

European Search Report for EP 14155802.3, dated Jul. 31, 2014.
International Search Report and Written Opinion for PCT/EP2014/078229, dated Apr. 14, 2015.
Eckardt, Physikalische Messungen an Filmbildnern Fur Haarsprays (Physical Measurements of Film Formers Useful for Hair Sprays), Journal of Society Cosmetic Chemists, U.S. vol. 21, No. 5, Jan. 1, 1970, pp. 281-287, XP002094847, ISSN: 0037-9832, p. 282, paragraph 2.

\* cited by examiner

*Primary Examiner* — Susan T Tran
(74) *Attorney, Agent, or Firm* — Sandra B. Weiss

(57) ABSTRACT

A hair fixative composition includes at least one carboxylated cellulose ether based polyglucose polymer, an alcohol based solvent system, and a cosmetically acceptable additive, wherein the polyglucose polymer is soluble in the alcohol based solvent system. The polyglucose polymer is obtained by reacting at least one cellulose ether with at least one anhydride.

15 Claims, No Drawings

HAIR FIXATIVES INCLUDING CELLULOSE ETHER BASED POLYGLUCOSE POLYMERS

This application is a national stage filing under 35 U.S.C. § 371 of PCT/EP2014/078229, filed Dec. 17, 2014, which claims priority to U.S. Provisional Patent Application No. 61/919,116 filed Dec. 20, 2013, and European Patent Application No. 14155802.3, filed Feb. 19, 2014, the contents of which are each incorporated herein by reference in their entireties.

FIELD OF THE INVENTION

The invention relates to hair fixative compositions comprising carboxylated cellulose ether based polyglucose polymers. More specifically, the invention relates to hair fixative compositions comprising carboxylated cellulose ether based polyglucose polymers that are soluble in alcohol based solvent systems.

BACKGROUND OF THE INVENTION

Polymers used in personal care applications, such as hair styling and hair fixing, have conventionally been made using synthetic materials. In order for the polymers to be suitable in such personal care applications, they must be soluble in alcohol based systems, and in the case of aerosol based hair sprays, they must also be compatible with the propellant. Conventional synthetic polymers are generally inexpensive and provide acceptable performance; however, because they are not made from renewable resources, they are not sustainable or suffer from other undesirable properties. For example, U.S. Pat. No. 3,741,783 discloses the use of ethyl cellulose ether based polymers for use in hair preparations. However, as described in this patent, the ethyl cellulose ethers are sulfated using a sulfating agent to produce sulfated alkali ether resins. The use of sulfate-containing ingredients is increasingly becoming undesirable in personal care compositions, as such ingredients are generally considered to lead to skin/scalp irritation, hair loss and/or hair thinning. Further, consumers are increasingly reluctant to purchase sulfate-containing hair care products due to potential safety concerns and allergic reactions towards such chemicals.

Accordingly, there is a need for personal care polymers made from renewable sources that provide equal to or better performance at comparable costs than their synthetic alternatives and that are soluble in alcohol based systems, such as ethanol based systems, that are also made from non-sulfate-containing materials. Further, such personal care polymers must also, if utilized in aerosol based hairsprays, they must also be compatible with propellants, such as dimethyl ether.

SUMMARY OF THE INVENTION

In an aspect, the present invention relates to a hair fixative composition comprising at least one carboxylated cellulose ether based polyglucose polymer; an alcohol based solvent system; and a cosmetically acceptable additive. The polyglucose polymer is obtained by reacting at least one cellulose ether with an anhydride, preferably a cyclic anhydride, and the polyglucose polymer is soluble in the alcohol based solvent system.

In another aspect, the present invention relates to a method of preparing a hair fixative composition comprising reacting at least one cellulose ether with an anhydride, preferably a cyclic anhydride, to form a cellulose ether based polyglucose polymer. In a further step, the method comprises dissolving or suspending the cellulose ether based polyglucose polymer in the alcohol based solvent.

In yet another aspect, the present invention relates to the use of the carboxylated cellulose ether based polyglucose polymer as defined herein as a hair fixative polymer in a hair fixative composition, as well as a method of styling hair, comprising applying the carboxylated cellulose ether based polyglucose polymer as defined herein to hair.

DETAILED DESCRIPTION OF THE INVENTION

As used herein, the recitations of numerical ranges by endpoints include all numbers subsumed within that range (e.g., 1 to 5 includes 1, 1.5, 2, 2.75, 3, 3.80, 4, 5, etc.). In addition, it is to be understood that for embodiments including ranges as described herein, the respective lower endpoints and respective upper endpoints described include combinations of the various lower and upper endpoints. For example, for ranges of 1 to 20 and 5 to 10, respectively, the ranges also include, without limitation, 1 to 10 and 5 to 20.

The hair fixative compositions of the present invention comprise carboxylated cellulose ether based polyglucose polymers that combine the features of having a carboxylated cellulose ether backbone having attached at least one short chain alkyl chain length ether (e.g. $C_1$-$C_4$ alkyl ether) and/or at least one alkoxylate group and at least one carboxyl functional group attached.

It has been found that the carboxylated cellulose ether based polyglucose polymers can provide hair fixative polymers that are not only made from renewable sources but that can also provide equal to or better hair styling performance, such as spray rate, viscosity, stiffness and high humidity curl retention, especially as hair spray polymers, at comparable costs to their synthetic alternatives. The inventive polymers are soluble in an alcohol based solvent system and, optionally, they are also compatible with hair styling propellants.

The present invention generally relates to hair fixative compositions including at least one carboxylated cellulose ether based polyglucose polymer having the following structure (I):

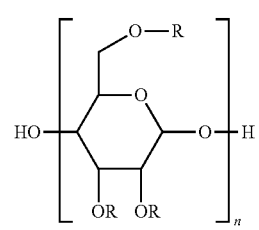

I wherein R=H, $R_H$ or $R_A$ or combinations thereof, wherein at least one R is $R_A$ and wherein $R_H$ is: (a) a $C_1$-$C_{22}$ alkyl group, preferably a $C_1$ to $C_{10}$ alkyl group, and more preferably a $C_1$-$C_4$ group; (b) a —CH2-CH2-$OR^1$ group, wherein $R^1$=—$CH_3$ or —$CH_2$—$CH_3$; or (c) a —$CH_2$—CH($CH_3$)—$OR^2$ group, wherein $R^2$=—$CH_3$ or —$CH_2$—$CH_3$; and $R_A$ is: (d) —CO—$CH_2$—CH($R^3$)—COOH wherein $R^3$=H or a $C_1$-$C_{18}$ alkyl or alkenyl group, preferably a $C_6$ to $C_{18}$ alkyl group, and more preferably a $C_8$, $C_{12}$ or $C_{18}$ alkenyl group; e) —CO—CH=CH—COOH; f) —CO—CH—C(=$CH_2$)—COOH; g) —CO—$C_6H_4$—COOH or h) —CO—$C_6H_8$—COOH; and wherein n=10-500, preferably 20-400 and more preferably 30-100. Combinations of (a), (b) and (c) with (d), (e), (f), (g) and/or (h) are also included. The hair fixative compositions further include an alcohol based solvent system and a cosmetically acceptable additive, wherein the polyglucose polymer is soluble in the alcohol based solvent system.

In the above formula (I), $R_H$ represents hydrophobic groups and $R_A$ represents groups having acid functionality and, optionally, hydrophobic functionality. In general, the cellulose ether based polyglucose polymers are formed by reacting an ether of a polysaccharide, such as, methyl cellulose, ethyl cellulose, methyl hydroxyethyl cellulose, methyl hydroxypropyl cellulose, ethyl cellulose and ethyl hydroxypropyl cellulose with an anhydride, such as an acyclic anhydride or a cyclic anhydride. In an embodiment, the anhydride is preferably a cyclic anhydride. In another embodiment, the anhydride may be a substituted anhydride or an unsubstituted anhydride. In a further embodiment, the anhydride is more preferably a substituted anhydride. Suitable cyclic anhydrides include, but are not limited to, a succinic anhydride, or alkenyl succinic anhydride or maleic anhydride or itaconic anhydride, or phthalic anhydride, or tetrahydrophthalic anhydride to give a succinate derivative, a maleate derivative, an itaconate derivative, a phthalate derivative, a tetrahydrophthalate derivative or combinations thereof. In one embodiment, the cyclic anhydride is a non-aromatic anhydride. In a further embodiment, suitable non-aromatic cyclic anhydrides include, but are not limited to, a succinic anhydride, or alkenyl succinic anhydride or maleic anhydride or itaconic anhydride, to give a succinate derivative, a maleate derivative, an itaconate derivative, or combinations thereof.

In an embodiment, the weight ratio of $R_H:R_A$ is from about 1:6 to about 1.5:1, in another embodiment preferably from about 1:4 to about 1:1.2, and in yet another embodiment from about 1:2.3 to about 1:1.

In an embodiment of the present invention, the polysaccharide ether may be modified with an anhydride in an amount from about 15 wt % to about 60 wt % based on weight percent of the polysaccharide ether. In another embodiment, the polysaccharide ether preferably may be modified with the anhydride in an amount from about 20 wt % to about 55 wt %, and in yet another embodiment, more preferably from about 30 wt % to about 50 wt %.

Non-limiting examples of carboxylated cellulose ester based polyglucose polymers according to the invention include polymers of formula (I) wherein $R_H$ is: (a) a $C_1$-$C_{22}$ alkyl group, preferably a $C_1$ to $C_{10}$ alkyl group, and more preferably a $C_1$-$C_4$ group and $R_A$ is: (d) —CO—CH$_2$—CH(R$^3$)—COOH wherein R$^3$=H or a $C_1$-$C_{18}$ alkyl or alkenyl group, preferably a $C_6$ to $C_{18}$ alkyl group, and more preferably a $C_8$, $C_{12}$ or $C_{18}$ alkenyl group, and wherein n=10-500, preferably 20-400 and more preferably 30-300; wherein $R_H$ is: (a) a $C_1$-$C_{22}$ alkyl group, preferably a $C_1$ to $C_{10}$ alkyl group, and more preferably a $C_1$-$C_4$ group and $R_A$ is: e) —CO—CH=CH—COOH, wherein n=10-500, preferably 20-400 and more preferably 30-300; wherein $R_H$ is: (a) a $C_1$-$C_{22}$ alkyl group, preferably a $C_1$ to $C_{10}$ alkyl group, and more preferably a $C_1$-$C_4$ group and $R_A$ is: f) —CO—CH—C(=CH$_2$)—COOH, wherein n=10-500, preferably 20-400 and more preferably 30-300; wherein $R_H$ is: (a) a $C_1$-$C_{22}$ alkyl group, preferably a $C_1$ to $C_{10}$ alkyl group, and more preferably a $C_1$-$C_4$ group and $R_A$ is: g) —CO—$C_6H_4$—COOH; and wherein n=10-500, preferably 20-400 and more preferably 30-300; wherein $R_H$ is: (a) a $C_1$-$C_{22}$ alkyl group, preferably a $C_1$ to $C_{10}$ alkyl group, and more preferably a $C_1$-$C_4$ group and $R_A$ is: h) —CO—$C_6H_8$—COOH; wherein $R_H$ is: (b) a —CH2-CH2-OR$^1$ group, wherein R$^1$=—CH$_3$ or —CH$_2$—CH$_3$ and $R_A$ is: (d) —CO—CH$_2$—CH(R$^3$)—COOH wherein R$^3$=H or a $C_1$-$C_{18}$ alkyl or alkenyl group, preferably a $C_6$ to $C_{18}$ alkyl group, and more preferably a $C_8$, $C_{12}$ or $C_{18}$ alkenyl group, and wherein n=10-500, preferably 20-400 and more preferably 30-300; wherein $R_H$ is: (b) a —CH2-CH2-OR$^1$ group, wherein R$^1$=—CH$_3$ or —CH$_2$—CH$_3$ and $R_A$ is: e) —CO—CH=CH—COOH, wherein n=10-500, preferably 20-400 and more preferably 30-300; wherein $R_H$ is: (b) a —CH2-CH2-OR$^1$ group, wherein R$^1$=—CH$_3$ or —CH$_2$—CH$_3$ and $R_A$ is: f) —CO—CH—C(=CH$_2$)—COOH, wherein n=10-500, preferably 20-400 and more preferably 30-300; or $R_H$ is: (b) a —CH2-CH2-OR$^1$ group, wherein R$^1$=—CH$_3$ or —CH$_2$—CH$_3$ and $R_A$ is: g) —CO—$C_6H_4$—COOH, wherein n=10-500, preferably 20-400 and more preferably 30-50; wherein $R_H$ is: (b) a —CH2-CH2-OR$^1$ group, wherein R$^1$=—CH$_3$ or —CH$_2$—CH$_3$ and $R_A$ is: h) —CO—$C_6H_8$—COOH, wherein n=10-500, preferably 20-400 and more preferably 30-300; wherein $R_H$ is: (c) a —CH$_2$—CH(CH$_3$)—OR$^2$ group, wherein R$^2$=—CH$_3$ or —CH$_2$—CH$_3$ and $R_A$ is: (d) —CO—CH$_2$—CH(R$^3$)—COOH wherein R$^3$=H or a $C_1$-$C_{18}$ alkyl or alkenyl group, preferably a $C_6$ to $C_{18}$ alkyl group, and more preferably a $C_8$, $C_{12}$ or $C_{18}$ alkenyl group, wherein n=10-500, preferably 20-400 and more preferably 30-300; wherein $R_H$ is: (c) a —CH$_2$—CH(CH$_3$)—OR$^2$ group, wherein R$^2$=—CH$_3$ or —CH$_2$—CH$_3$ and $R_A$ is: e) —CO—CH=CH—COOH, wherein n=10-500, preferably 20-400 and more preferably 30-300; wherein $R_H$ is: (c) a —CH$_2$—CH(CH$_3$)—OR$^2$ group, wherein R$^2$=—CH$_3$ or —CH$_2$—CH$_3$ and $R_A$ is: f) —CO—CH—C(=CH$_2$)—COOH, wherein n=10-500, preferably 20-400 and more preferably 30-300; wherein $R_H$ is: (c) a —CH$_2$—CH(CH$_3$)—OR$^2$ group, wherein R$^2$=—CH$_3$ or —CH$_2$—CH$_3$ and $R_A$ is: g) —CO—$C_6H_4$—COOH, wherein n=10-500, preferably 20-400 and more preferably 30-300; wherein $R_H$ is: (c) a —CH$_2$—CH$_2$—OR$^1$ group, wherein R$^1$=—CH$_3$ or —CH$_2$—CH$_3$ and $R_A$ is: h) —CO—$C_6H_8$—COOH, wherein n=10-500, preferably 20-400 and more preferably 30-300. In an embodiment, combinations of the above are also included.

Examples of carboxylated cellulose ether based polyglucose polymers suitable for use in the present invention include, but are not limited to, methyl cellulose succinate, ethyl cellulose succinate, methyl hydroxyethyl cellulose succinate, methyl hydroxypropyl cellulose succinate, ethyl hydroxypropyl cellulose succinate, methyl cellulose alkenyl succinate, ethyl cellulose alkenyl succinate, methyl hydroxyethyl cellulose alkenyl succinate, methyl hydroxypropyl cellulose alkenyl succinate, ethyl hydroxypropyl cellulose alkenyl succinate, methyl cellulose maleate, ethyl cellulose maleate, methyl hydroxyethyl cellulose maleate, methyl hydroxypropyl cellulose maleate, ethyl hydroxypropyl cellulose maleate, methyl cellulose itaconate, ethyl cellulose itaconate, methyl hydroxyethyl cellulose itaconate, methyl hydroxypropyl cellulose itaconate, ethyl hydroxypropyl cellulose itaconate, methyl cellulose phthalate, ethyl cellulose phthalate, methyl hydroxyethyl cellulose phthalate, methyl hydroxypropyl cellulose phthalate, ethyl hydroxypropyl cellulose phthalate, methyl cellulose tetrahydrophthalate, ethyl cellulose tetrahydrophthalate, methyl hydroxyethyl cellulose tetrahydrophthalate, methyl hydroxypropyl cellulose tetrahydrophthalate, ethyl hydroxypropyl cellulose tetrahydrophthalate or combinations thereof.

In another embodiment, examples of carboxylated cellulose ether based polyglucose polymers suitable for use in the present invention include, but are not limited, to methyl cellulose succinate, ethyl cellulose succinate, methyl hydroxyethyl cellulose succinate, methyl hydroxypropyl cellulose succinate, ethyl hydroxypropyl cellulose succinate, methyl cellulose alkenyl succinate, ethyl cellulose alkenyl succinate, methyl hydroxyethyl cellulose alkenyl succinate, methyl hydroxypropyl cellulose alkenyl succinate, ethyl hydroxypropyl cellulose alkenyl succinate, methyl cellulose maleate, ethyl cellulose maleate, methyl hydroxyethyl cellulose maleate, methyl hydroxypropyl cellulose maleate, ethyl hydroxypropyl cellulose maleate, methyl cellulose itaconate, ethyl cellulose itaconate, methyl hydroxyethyl cellulose itaconate, methyl hydroxypropyl cellulose itaconate, and ethyl hydroxypropyl cellulose itaconate, and combinations thereof.

In an embodiment, the cellulose based polyglucose polymers of the present invention may be present in the hair fixative composition in an amount from about 1 weight percent to about 10 weight percent, based on the weight of the hair fixative composition. In another embodiment, the polyglucose polymers are present in an amount from about 2 weight percent to about 8 weight percent. In yet another embodiment, the polyglucose polymers are present in an amount from about 3 weight percent to about 6 weight percent.

The polyglucose polymers of the present invention may be based on cellulose or cellulose derivatives. Cellulose is a polysaccharide composed of individual anhydroglucose units which are linked through a glycosidic bond. Typically, production of cellulose derivatives involves replacing some of the hydroxyl hydrogen groups of cellulose with a substituent group. The number of substituted hydroxyl groups per anhydroglucose unit is expressed as the degree of substitution (D.S.). As reported in more detail in U.S. Pat. No. 6,841,232, which is incorporated by reference in its entirety herein, D.S. can vary from 0 to 3. In one embodiment, the polyglucose polymers of the invention have a total D.S. of at least 2.

Examples of polyglucose polymers based on cellulose ethers suitable for use in the present invention include, without limitation, $C_1$-$C_4$ alkyl ethers, and in an embodiment, more preferably $C_1$ or $C_2$ alkyl ethers and/or alkoxylates, and in another embodiment, more preferably ethoxylates and propoxylates. Mixtures of these ether derivatives may also be included. In a preferred embodiment, the $C_1$-$C_4$ alkyl ethers include methyl ethers, ethyl ethers and n-propyl ethers.

Examples of suitable cellulose ethers used as starting materials include but are not limited to methy cellulose, ethyl cellulose, propyl cellulose, butyl cellulose, methylhydroxyethylcellulose, methylethylhydroxyethyl cellulose, ethylhydroxyethylcellulose, hydroxypropylmethylcellulose, hydroxypropylethylcellulose, hydrophobically modified ethylhydroxyethylcellulose, hydroxyethylcellulose, and mixtures thereof. Embodiments of the invention may also include modified versions of the cellulose ethers and mixtures thereof, including those that are hydrophobically modified. In an embodiment, methy cellulose, ethyl cellulose, methylhydroxyethylcellulose, hydroxypropylmethyl cellulose or mixtures thereof is preferred. The cellulose ethers can be prepared from any cellulose source, including, but not limited to, hardwood pulp, softwood pulp, cotton linters, bacterial cellulose, and regenerated cellulose.

In another aspect, the hair fixative compositions comprise at least one polyglucose polymer and an alcohol based solvent system. As used herein, an alcohol based solvent system comprises at least one alcohol and may include further optional components, such as water, propellant, or other non-alcohol, non-aqueous solvents. The polyglucose polymer must be soluble in the alcohol based solvent system. In an embodiment, the amount of alcohol present in the solvent system may be about 1 weight percent or greater, in another embodiment preferably about 15 weight percent or greater, and in yet another embodiment, more preferably from about 25 weight percent or greater. In an embodiment, the amount of alcohol present in the solvent system may be about 99 weight percent or less, in another embodiment preferably about 50 weight percent or less and in yet another embodiment more preferably about 40 weight percent or less, based on total weight of the solvent system. In another embodiment, the alcohol solvent system may be anhydrous.

In an embodiment of the invention, the hair fixative composition will include no more than about 85% volatile organic compounds (VOC), such as alcohol and/or propellant with the remainder of the solvent being water. In another embodiment, the hair fixative compositions will comprise no more than about 55% volatile organic compounds.

For purposes of the present invention, the term "soluble" means that from about 1 to about 10 weight percent, in another embodiment, preferably from about 3 to about 6 weight percent of the polyglucose polymer is soluble, with or without neutralization, in the alcohol based solvent system. In an embodiment, alcohol based solvent systems suitable for use in the present invention comprise at least one $C_1$-$C_6$ straight or branched chain alcohol or mixtures thereof and, optionally, water, optionally one or more propellants and optionally one or more other non-alcohol, non-aqueous solvents. In an embodiment, the alcohol based solvent system preferably includes at least one $C_2$ or $C_3$ alcohol or mixtures thereof.

In an embodiment of the invention, the hair fixative compositions optionally further include at least one neutralizing agent. In an embodiment of the invention, the polyglucose polymer is generally at least about 70% neutralized. In another embodiment, the polyglucose polymer is at least about 80% neutralized, and in an even further embodiment, the fixative polymer is 100% neutralized. Suitable basic neutralizing agents compatible with the composition can be employed, even inorganic materials such as sodium or potassium hydroxide. Generally organic amines or alkanolamines are readily used for neutralization. In an embodiment, the neutralizing agents include, but are not limited to ammonia; primary, secondary and tertiary amines; alkanolamines; and, hydroxyamines such as 2-amino-2-methylpropanol and 2-amino-2-methyl-1,3-propanediol, mono-, di- and tri-long chain fatty amines containing a $C_4$ to $C_{24}$ hydrocarbon chain, ethoxylates and propoxylates long chain ($C_4$ to $C_{24}$) fatty amines and mixtures thereof. In another embodiment, the neutralizing agents include aminomethylpropanol, and di-methyl stearamine, inorganic materials, such as sodium hydroxide and potassium hydroxide, and triethanolamine. In an embodiment of the invention, the neutralizing agent is an organic amine or alkanolamine. In an embodiment, combinations of neutralizing agents may also be used.

In an embodiment, the hair fixative compositions have spray rate in a range from about 0.3 to about 1.5 grams/sec. in an 80% VOC system at 5% solids and 40% DME, in another embodiment, preferably from about 0.5 grams/sec. to about 1.2 grams/sec., and in another embodiment, more preferably from 0.75 about to 0.9 grams/sec.

In addition to the above-described solvent systems, the present invention may further optionally include one or more propellants. In an embodiment of the invention where the hair fixative composition is a spray application, the polyglucose polymer is compatible with the propellant. By compatible, it is meant that the polyglucose polymer in the solvent system does not phase separate when the solution is mixed with the propellant. In an embodiment, the polyglucose polymer is preferably compatible with dimethyl ether as the propellant. For purposes of the present invention, the term "compatible" means that up to about 10 weight percent of the polyglucose polymer is soluble in the hair fixative composition that includes the propellant. In another embodiment, the polyglucose polymer is preferably soluble from about 1 to about 10 weight percent, and in yet another embodiment, from about 2 to about 8 weight percent and in still yet another embodiment from about 3 to about 6 weight percent in the hair fixative composition that includes the propellant.

Spray applications of the present invention require a mechanical device or pressurized aerosol container to generate the spray. The devices can be manual such as a pump or squeeze bottle or typical aerosol device such as bag-on-nozzle or pressurized can. If a pressurized can is used then the hair styling formulations of the present invention may further include a propellant. Such propellants include, without limitation, ethers, such as dimethyl ether; one or more lower boiling hydrocarbons such as $C_3$-$C_6$ straight and branched chain hydrocarbons, for example, propane, butane, and isobutane; halogenated hydrocarbons, such as, hydrofluorocarbons, for example, trichlorofluoromethane, dichlorodifluoromethane, 1,1-difluoroethane and 1,1,1,2-tetrafluoroethane, present as a liquefied gas; and the compressed gases, for example, nitrogen, air and carbon dioxide as well as mixtures of these propellants. In an embodiment of the invention, the propellant is present in an amount of about 25% to about 80% by weight of the hair fixative composition including the solvent system. In a further embodiment, the propellant is present in an amount of about 30% to about 60% by weight. Alternatively, in certain spray applications, such as bag-on-nozzle spray applications or pump spray applications, such optional propellants are not required. The hair fixative compositions of the present invention include, but are not limited, to aerosol and non-aerosol hairsprays.

In general, in another aspect of the invention, the method for preparing the hair spray formulations of this invention includes involves dissolving, suspending or diluting the polyglucose polymer in the selected solvents, adding any modifying agents depending on the desired properties, and thereupon combining the resulting solution with the selected aerosol propellant.

With regard to amounts of the various components, in an embodiment the hair fixative compositions of the present invention may contain the carboxylated cellulose ether based polyglucose polymer in a concentration ranging from about 1 to 10%, by weight; the alcohol based solvent system in a concentration ranging from about 30 to 90%, by weight; and, optionally, the propellant concentration in a range from 20 to 75%, by weight. In another embodiment the hair fixative compositions of the present invention may contain the polyglucose polymer in a concentration ranging from about 2 to 8%, by weight; the solvent in a concentration ranging from about 25 to 55%, by weight; and, if included, the optional propellant concentration in a range from 25 to 55%, by weight.

In yet another aspect, the present invention relates to the use of the carboxylated cellulose ether based polyglucose polymer as defined herein as a hair fixative polymer in a hair fixative composition, as well as a method of styling hair, comprising applying the carboxylated cellulose ether based polyglucose polymer as defined herein to hair. In one embodiment the hair fixative composition is in the form of a spray, in one embodiment the spray is an aerosol spray, in one embodiment the spray is a non-aerosol spray. In one embodiment the hair fixative composition is in the form of a mousse. In one embodiment the hair fixative composition is in the form of a gel.

The application of the hair styling formulations of the present invention may be prior to, during, or after the desired hair style has been achieved.

Optionally, cosmetically acceptable additives may be incorporated into the hair fixative compositions of this invention in order to modify certain properties thereof. One such optional additive may, in additional to the polyglucose polymer, a second polymer, such as a hair fixative polymer. Non-limiting examples of these additional hair fixative polymers include: from Akzo Nobel Surface Chemistry LLC, AMPHOMER® 4961, AMPHOMER®, and AMPHOMER® LV-71 polymers (octylacrylamide/acrylates/butylaminoethyl methacrylate copolymer), AMPHOMER® HC polymer (acrylates/octylacrylamide copolymer) and BALANCE® CR polymers (acrylates copolymer), BALANCE® 47 polymer (octylacrylamide/acrylates/butylaminoethyl methacrylate copolymer), RESYN® 28-2930 polymer (VA/crotonates/vinyl neodecanoate copolymer), RESYN® 28-1310 polymer (VA/Crotonates copolymer), FLEXAN® polymers (sodium polystyrene sulfonate), DynamX polymer (polyurethane-14 (and) AMP-Acrylates copolymer), RESYN® XP polymer (acrylates/octylacrylamide copolymer), STRUCTURE® 2001 (acrylates/steareth-20 itaconate copolymer) and STRUCTURE® 3001 (acrylates/ceteth-20 itaconate copolymer); from Ashland Inc., OMNIREZ-2000® (PVM/MA half ethyl ester copolymer), GANEX P-904® (butylated PVP), GANEX V-216® (PVP/hexadecene copolymer) GANEX® V-220 (PVP/eicosene copolymer), GANEX® WP-660 (tricontanyl PVP), GANTREZ® A425 (butyl ester of PVM/MA copolymer), GANTREZ® AN-119 PVM/MA copolymer, GANTREZ® ES 225 (ethyl ester of PVM/MA copolymer), GANTREZ® ES425 (butyl ester of PVM/MA copolymer), GAFFIX® VC-713 (vinyl caprolactam/PVP/dimethylaminoethyl methacrylate copolymer), GAFQUAT® 755 (polyquatemium-11), GAFQUAT® HS-100 (polyquatemium-28) AQUAFLEX® XL-30 (Polyimide-1), AQUAFLEX® SF-40 (PVP/Vinylcaprolactam/DMAPA Acrylates Copolymer), AQUAFLEX® FX-64 (Isobutylene/Ethylmaleimide/Hydroxyethylmaleimide Copolymer), ALLIANZ® LT-120 (Acrylates/C1-2 Succinates/Hydroxyacrylates Copolymer), STYLEZE® CC-10 (PVP/DMAPA Acrylates Copolymer), STYLEZE® 2000 (VP/Acrylates/Lauryl Methacrylate Copolymer), STYLEZE® W-20 (Polyquaternium-55), Copolymer Series (PVP/Dimethylaminoethylmethacrylate Copolymer), ADVANTAGE® S and ADVANTAGE® LCA (VinylcaprolactamNP/Dimethylaminoethyl Methacrylate Copolymer), ADVANTAGE® PLUS (VA/Butyl Maleate/Isobornyl Acrylate Copolymer); from BASF, The Chemical Company, ULTRAHOLD STRONG (acrylic acid/ethyl acrylate/t-butyl acrylamide), LUVIMER® 100P (t-butyl acrylate/ethyl acrylate/methacrylic acid), LUVIMER® 36D (ethyl acrylate/t-butyl acrylate/methacrylic acid), LUVIQUAT® HM-552 (polyquaternium-16), LUVIQUAT® HOLD (polyquatemium-16), LUVISKOL® K30 (PVP) LUVISKOL® K90 (PVP), LUVISKOL® VA 64 (PVP/VA copolymer) LUVISKOL® VA73W (PVP/VA copolymer), LUVISKOL® VA, LUVISET® PUR (Polyurethane-1), LUVISET® Clear (VP/Methacrylamide/Vinyl Imidazole Copolymer), LUVI- FLEX® SOFT (Acrylates Copolymer), ULTRAHOLD® 8 (Acrylates/Acrylamide Copolymer), LUVISKOL® Plus (Polyvinylcaprolactam), LUVIFLEX® Silk (PEG/PPG-25/25 Dimethicone/Acrylates Copolymer); from The Dow Chemical Company, ACUDYNE® 180, ACUDYNE® 1000, and ACUDYNE® DHR (Acrylates/Hydroxyesters Acrylates Copolymer), ACUDYNE® SCP (Ethylenecarboxyamide/AMPSA/Methacrylates Copolymer), and the ACULYN® rheological modifiers; from Mitsubishi and distributed by Clariant Corporation, DIAFORMER® Z-301, DIAFORMER® Z-SM, and DIAFORMER® Z-400 (methacryloyl ethyl betaine/acrylates copolymer), from Nalco Company, FIXOMER® A-30 and FIXOMER® N-28 (INCI names: methacrylic acid/sodium acrylamidomethyl propane sulfonate copolymer); from tThe Lubrizol Corporation, FIXATE® G-100 (AMP-Acrylates/Allyl Methacrylate Copolymer), FIXATE PLUS® (Polyacrylates-14), FIXATE® SUPERHOLD (Polyacrylate-2 Crosspolymer), and FIXATE® FREESTYLE (Acrylates Crosspolymer-3) CARBOPOL® Ultrez 10 (Carbomer), CARBOPOL® Ultrez 20 (Acrylates/C10-30 Alkyl Acrylates Copolymer), AVALURE® AC series (Acrylates Copolymer), AVALURE® UR series (Polyurethane-2, Polyurethane-4, PPG-17/IPDI/DMPA Copolymer); polyethylene glycol; water-soluble acrylics; water-soluble polyesters; polyacrylamides; polyamines; polyquaternary amines; styrene maleic anhydride (SMA) resin; polyethylene amine; and other conventional polymer that is polar solvent soluble or that can be made soluble through neutralization with the appropriate base. A combination of one or more of the above hair fixative polymers is also contemplated as within the scope of the present invention. In an embodiment of the invention, the hair fixative polymer is preferably chosen from octylacrylamide/acrylates/butylaminoethyl methacrylate copolymers, acrylates/octylacrylamide copolymers, acrylates copolymer, octylacrylamide/acrylates/butylaminoethyl methacrylate copolymers, VA/crotonates/vinyl neodecanoate copolymers, VA/Crotonates copolymers, sodium polystyrene sulfonates, polyurethane-14 (and) AMP-Acrylates copolymers, acrylates/octylacrylamide copolymers, acrylates/steareth-20 itaconate copolymers, acrylates/ceteth-20 itaconate copolymers and combinations thereof.

In an embodiment of the invention, the optional hair fixative polymer may be present in the hair fixative composition in an amount of about 0.1 to 10% by weight based on total weight of the composition. In a further embodiment, the fixative polymer is present in an amount of about 1 to 10% by weight and in a further embodiment in an amount of about 1 to 7% by weight.

Further optional cosmetically acceptable additives may also include: plasticizers, such as glycols, phthalate esters and glycerine; silicones; emollients, lubricants and penetrants such as lanolin compounds, protein hydrolyzates and other protein derivatives, ethylene oxide adducts, and polyoxyethylene cholesterol; UV absorbers; dyes and other colorants; and, perfumes. Mixtures of these optional additives may also be included. As previously noted, the polymeric binders of this invention show little or no tendency to adversely chemically interact with such additives.

Further optional ingredients can include, but are not limited to, preservatives, colorants, fragrances, viscosity modifiers, vitamins, herbal extracts such as sterols, triterpenes, flavonoids, coumarins, non-glycosidic diterpenes (sterebins) spathulenol, decanoic acid, 8,11,14-ecosatrienoic acid, 2-methyloctadecane, pentacosane, octacosane, stigmasterol, bsitosterol, a- and b-amyrine, lupeol, b-amyrin acetate, and pentacyclic triterpene, include sunscreen actives such as such as a p-methoxycinnamate or an aminobenzoate (UVB absorber) or benzone or an anthranilate (UVA absorber medicaments, moisturizers, anti-itch or anti-dandruff ingredients and the like.

The resulting hair fixative formulations exhibit the characteristics required of such a product. They possess good antistatic properties, adhere well to hair, are easily removed by soapy water or shampoos, allow the hair to be readily recombed, do not yellow on aging, do not become tacky when exposed to high humidities, and have excellent curl retention under high humidity conditions.

The method for preparing the hair fixative compositions of the present invention can be performed in a number of different ways, and depends on the polyglucose polymer used. However, in a further aspect of the invention, the invention provides a non-limiting method for preparing a hair fixative composition. The method comprises suspending or dissolving the polyglucose polymer in an alcohol based solvent systems, for example comprising one or more $C_1$-$C_6$ alcohols. In an embodiment, the method may further include neutralizing the solution with a neutralizing agent, such as aminomethylpropanol. In an embodiment, the one or more alcohols may comprise ethanol in combination with isopropanol or n-propanol, optionally in a weight ratio of about 80:20 to about 20:80 ethanol to isopropanol. In yet another embodiment, optionally, the method further includes the step of adding propellant to the composition. In a further optional step, the method may also include adding water to the composition either before, during, or after suspending the polyglucose polymer in the alcohol or after the neutralizing step.

In an embodiment, the polyglucose polymers of the present invention are suitable for use in hair fixative compositions, such as hair sprays, mousses or gels.

The following examples are intended to exemplify the present invention but are not intended to limit the scope of the invention in any way. The breadth and scope of the invention are to be limited solely by the claims appended hereto.

EXAMPLES

A. Synthesis Method for Polyglucose Polymers

Ethyl Cellulose

For the reaction of ethyl cellulose with an anhydride, a reaction vessel equipped with an agitator and condenser was kept under nitrogen atmosphere and immersed in an oil bath for heating. The reactor was charged with weighed amounts of ethyl cellulose (ETHOCEL™ Std. 4 ethyl cellulose from The Dow Chemical Company), acetic acid, sodium acetate and succinic anhydride (or maleic anhydride), as shown in Table 1, with the amounts in grams. The mixture was heated to 95° C. under stirring until the reaction showed completion as monitored by IR for the disappearance of the anhydride peak. The reaction mixture was then cooled to about 60° C. and water (about 5-8 times the total weight of the substrates) was slowly added to this reaction mixture under vigorous stirring. After stirring for 30 min., the solid separated was filtered, washed with water until all the residual acetic acid was washed off and dried in oven at 45° C. overnight to give a solid product. The acidity value was measured and a determination was made as to whether the polymer was soluble in ethanol.

TABLE 1

Reactions with Ethyl Cellulose

| Example | EC | AA | NaOAc | SA | MA | Acidity Mg KOH/g (meq/g) | EtOH sol. (product) 5 wt % |
|---|---|---|---|---|---|---|---|
| 3 (15% SA) | 10 | 15 | 8 (0.098) | 1.5 (0.015) |  | 12.9 (0.23) | Soluble |
| 1 (25% SA) | 10 | 15 | 8 (0.098) | 2.5 (0.025) |  | 34.2 (0.61) | Soluble |
| 6 (30% SA) | 30 | 45 | 24 (0.293) | 9 (0.09) |  | 71.8 (1.28) | Soluble |
| 2 (40% SA) | 10 | 15 | 8 (0.098) | 4 (0.04) |  | 81.3 (1.45) | Soluble |
| 5 (2354-40) (50% SA) | 20 | 30 | 16 (0.195) | 10 (0.10) |  | 78.5 (1.4) | Soluble |
| 4 (40% MA) | 10 | 15 | 8 (0.098) |  | 4 (0.41) | 1.01 | Soluble |

All Examples used ETHOCEL STD 4 available from The Dow Chemical Company.
AA = acetic acid;
NaOAc = sodium acetate;
SA = succinic anhydride;
MA = maleic anhydride.

As shown in Table 1, all of the samples, despite different levels of succinic anhydride or maleic anhydride treatment, were found to be soluble in ethanol even without any neutralization.

B. Subjective Test Procedures

The following procedures were used to conduct the subjective evaluations.
Gloss:
Gently handle the swatches so as not to break the films. Visually inspect the swatches to determine which has more shine/gloss.
Stiffness:
Gently handle swatches and feel for differences in stiffness. Using two fingers, hold the middle of the swatch in a horizontal position—does one bend more than the other? Choose the one that is more rigid.
Spring:
While holding the swatch in one hand, gently pull on an edge with the other hand three times only. Look for spring back, and bounce. The more elastic the better the Spring.
Webbing:
While holding the swatch in both hands, gently pull outward on the edges approx. 4". (Do this three times only to avoid damage to the bonds. If the bonds are destroyed then the dry combing may appear to be easier to comb). The more net like the better the Webbing.
Dry Comb:
Comb through each swatch (5) times and evaluate ease of combing. Choose the one that combs more easily.
Flake:
Visually inspect both swatches after combing. Check the teeth of the comb for flake accumulation. Holding the swatch at the bound end run your fingernail down the length of the tress then inspect. Choose the one with more flakes.
Anti-Stat:
Holding swatch at bound end comb through vigorously 10 times then evaluate for extent of fly aways generated. Choose the one with more fly aways.
Feel:
Handle swatches and determine preference. Choose the one that feels more silky/cleaner.

Example 8

Subjective Evaluations of Ethyl Cellulose Succinate Polymers

Subjective evaluations were performed on Example 5 and compared AMPHOMER® polymer, each using 5% polymer using 80% VOC ethanol-water and 40% DME using statistical design method at 80% confidence level. The results are reported in Table 2.

TABLE 2

| Example | Gloss | Stiffness | Spring | Webbing | Dry comb | Flake | Antistat | Feel |
|---|---|---|---|---|---|---|---|---|
| 5 | − | − | − | = | = | = | = | = |

= not statistically different;
+ superior;
− inferior

Based on the test results illustrated in Table 2, it can be seen that ethyl cellulose succinate polymer tested performed statistically the same as the synthetic polymer AMPHOMER® polymer in five of the eight categories.

C. Objective Evaluations

Determination of Spray Rate
Materials/Equipment:
Vented fume hood
Safety glasses
Top loading balance (0.01 gram accuracy)
Seconds' timer
\
PROCEDURE: Run In Duplicate
Aerosol Hair Spray
1 Weigh can of hair spray and record weight.
2. Place can in fume hood. Using constant pressure, depress actuator for ten seconds.
3. Re-weigh can and record weight.
Calculation: Initial Weight−Weight After Spraying=grams/second
Note: if duplicates do not agree to within 0.03 g/sec, repeat procedure
Non-Aerosol Hair Spray
1. Weigh pump bottle of hair spray and record weight.
2. Place bottle in fume hood. Consistently and completely, depress the actuator ten times ("bursts").
3 Re-weigh pump bottle and record weight.
Calculation: Initial Weight−Weight After Spraying=grams/"burst"
Note: if duplicates do not agree to within 0.03 g/"burst", repeat procedure Valve Specification (procured from a company called Aptar)
Product VX-81
Body: VX Barbed 0.013 NOVT ARIAN
Stem: VX80 0.343 FC 1×0.013 ORIFICE
GASKET: VX.045 BUTYL CODE 501
SPRING: VS STAINLESS STEEL 0.018 OPEN C
CUP: HIPRO BNA PGFR GSK AL EP T/B D
TUBE: 0.122 ID
TUBE LENGTH: 09 00/16"
Actuator Specification (from Aptar)
REF NO: XL002838
PRODUCT: XL200 SHIP OUT LABNUM: XL200 VX MISTY TAP 0.023 MISTY
BUTTON: VX XL 200 MISTY TAP WHITE
INSERT: 0.023 MISTY BLACK Example 9

Objective Evaluations of Ethyl Cellulose Succinate Polymers

Example 5 was screened for other properties and hairspray application as reported in Table 3 and compared to a conventional hairspray fixative polymer, AMPHOMER®, available from Akzo Nobel Surface Chemistry LLC. The objective evaluations were based on using 5 wt % of each of the polymers using 80 wt % VOC ethanol-water and 40 wt % DME at 90% neutralization using AMP.

TABLE 3

|  | pH of concentrate | Solubility in Ethanol after neutralization with AMP (5 wt % polymer) | Compatibility in 80% VOC ethanol system + 40% DME | Spray rate (g/sec) |
|---|---|---|---|---|
| Amphomer | 8.33 | soluble | soluble | 0.87 |
| Example 5 | 8.3 | soluble | soluble | 0.87 |

As shown in Table 3, Example 5 exhibited results comparable to AMPHOMER® polymer in all objective tests that were conducted.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described herein, the invention is not intended to be limited to the details shown. Rather, various modifications may be made in the details within the range and scope of equivalents of the claims and without departing from the spirit and scope of the invention.

I claim:

1. A hair fixative composition comprising:
    at least one carboxylated cellulose ether based polyglucose polymer obtained by reacting at least one cellulose ether with at least one cyclic anhydride;
    an alcohol based solvent system, wherein the alcohol based solvent system comprises at least one $C_1$-$C_6$ straight or branched chain alcohol, or mixtures thereof; and at least one cosmetically acceptable additive;
    wherein the at least one carboxylated cellulose ether based polyglucose polymer is soluble in the alcohol based solvent system, and
    wherein the at least one carboxylated cellulose ether based polyglucose polymer has the following structure

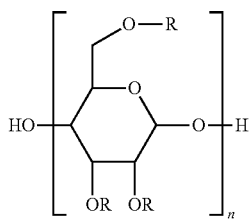

wherein R =H, $R_H$ or $R_A$ or combinations thereof, wherein at least one R is $R_A$, and
wherein $R_H$ is: (a) a $C_1$-$C_{22}$ alkyl group; (b) a —CH2—CH2—OR$^1$ group, wherein R$'$=—CH$_3$ or —CH$_2$—CH3; or (c) a —CH$_2$—CH(CH$_3$)—OR$^2$ group, wherein R$^2$=—CH$_3$ or —CH$_2$—CH$_3$; and $R_A$ is: (d) —CO—CH$_2$—CH(R$^3$)—COOH wherein R$^3$=H or a $C_1$-$C_{18}$ alkyl or alkenyl group; e) —CO—CH=CH—COOH; f) —CO—CH—C(=CH$_2$)—COOH; g) —CO—C$_6$H$_4$—COOH or h) —CO—C$_6$H$_8$—COOH; and
wherein n =10 -500.

2. The hair fixative composition of claim 1 wherein the at least one cellulose ether is a $C_1$-$C_4$ alkyl ether, an alkoxylate or a combination thereof.

3. The hair fixative composition of claim 1 wherein the at least one cellulose ether is selected from the group consisting of a methyl ether, ethyl ether, n-propyl ether, an ethoxylate, a propoxylate and combinations thereof.

4. The hair fixative composition of claim 1 wherein the at least one cellulose ether is selected from the group consisting of methyl cellulose, ethyl cellulose, methyl hydroxyethyl cellulose, methyl hydroxypropyl cellulose, ethyl hydroxypropyl cellulose and combinations thereof.

5. The hair fixative composition of claim 1 wherein the at least one cyclic anhydride comprises a substituted anhydride, an unsubstituted anhydride or a combination thereof.

6. The hair fixative composition of claim 1 wherein the at least one anhydride is selected from the group consisting of succinic anhydride, alkenyl succinic anhydride, maleic anhydride, itaconic anhydride, phthalic anhydride, tetrahydrophthalic anhydride and combinations thereof.

7. The hair fixative composition of claim 1 wherein the at least one carboxylated cellulose ether based polyglucose polymer is selected from the group consisting of methyl cellulose succinate, ethyl cellulose succinate, methyl hydroxyethyl cellulose succinate, methyl hydroxypropyl cellulose succinate, ethyl hydroxypropyl cellulose succinate, methyl cellulose alkenyl succinate, ethyl cellulose alkenyl succinate, methyl hydroxyethyl cellulose alkenyl succinate, methyl hydroxypropyl cellulose alkenyl succinate, ethyl hydroxypropyl cellulose alkenyl succinate, methyl cellulose maleate, ethyl cellulose maleate, methyl hydroxyethyl cellulose maleate, methyl hydroxypropyl cellulose maleate, ethyl hydroxypropyl cellulose maleate, methyl itaconate, ethyl cellulose itaconate, methyl hydroxyethyl cellulose itaconate, methyl hydroxypropyl cellulose itaconate, ethyl hydroxypropyl cellulose itaconate, methyl cellulose phthalate, ethyl cellulose phthalate, methyl hydroxyethyl cellulose phthalate, methyl hydroxypropyl cellulose phthalate, ethyl hydroxypropyl cellulose phthalate, methyl cellulose tetrahydrophthalate, ethyl cellulose tetrahydrophthalate, methyl hydroxyethyl cellulose tetrahydrophthalate, methyl hydroxypropyl cellulose tetrahydrophthalate, ethyl hydroxypropyl cellulose tetrahydrophthalate and combinations thereof.

8. The hair fixative composition of claim 1 wherein the alcohol based solvent system further comprises water, one or more propellants or one or more non-alcohol, non-aqueous solvents or mixtures thereof.

9. The hair fixative composition of claim 1 wherein the at least one carboxylated cellulose ether polyglucose polymer is present in the hair fixative composition in an amount from 1 weight percent to 10 weight percent, based on the weight of the hair fixative composition.

10. The hair fixative composition of claim 1 wherein the at least one carboxylated cellulose ether based polyglucose polymer is at least 70% neutralized.

11. The hair fixative composition of claim 1 wherein the at least one carboxylated cellulose ether based polyglucose polymer is sulfate-free.

12. The hair fixative composition of claim 1 wherein the hair fixative composition is an aerosol hairspray or a non-aerosol hairspray.

13. The hair fixative composition of claim 1 wherein the at least one cosmetically acceptable additive is selected from the group consisting of one or more second hair fixative polymers, plasticizers, UV absorbers, dyes, perfumes, preservatives, viscosity modifiers, vitamins, sunscreen actives, moisturizers, anti-itch or anti-dandruff ingredients and mixtures thereof.

14. A method of preparing a hair fixative composition of claim 1 comprising:
    reacting the at least one cellulose ether with the at least one cyclic anhydride to form the at least one cellulose ether based polyglucose polymer; and
    dissolving or suspending the at least one cellulose ether based polyglucose polymer in the alcohol based solvent system.

15. The hair fixative composition of claim 1 wherein said at least one $C_1$-$C_6$ straight or branched chain alcohol is selected from a $C_2$ or $C_3$ straight or branched chain alcohol.

* * * * *